(12) United States Patent
Moldoveanu et al.

(10) Patent No.: US 12,200,188 B2
(45) Date of Patent: Jan. 14, 2025

(54) TWO-DIMENSIONAL ULTRA SOUND TRANSDUCERS AND SYSTEMS

(71) Applicant: CLOUDSTREAM MEDICAL IMAGING, INC, Houston, TX (US)

(72) Inventors: Nicolae Moldoveanu, Houston, TX (US); Maurice Nessim, Houston, TX (US)

(73) Assignee: CLOUDSTREAM MEDICAL IMAGING, INC.

(*) Notice: Subject to any disclaimer, the term of this patent is extended or adjusted under 35 U.S.C. 154(b) by 0 days.

(21) Appl. No.: 18/227,681

(22) Filed: Jul. 28, 2023

(65) Prior Publication Data

US 2024/0163420 A1    May 16, 2024

Related U.S. Application Data

(63) Continuation-in-part of application No. PCT/US2023/017440, filed on Apr. 4, 2023, which is a continuation of application No. 17/712,919, filed on Apr. 4, 2022, now Pat. No. 11,663,759, application No. 18/227,681, filed on Jul. 28, 2023 is a continuation-in-part of application No. 17/993,699, filed on Nov. 23, 2022, now Pat. No. 11,893,734.

(51) Int. Cl.
| | |
|---|---|
| H04N 19/00 | (2014.01) |
| A61B 8/08 | (2006.01) |
| B06B 1/00 | (2006.01) |
| H03M 7/30 | (2006.01) |

(52) U.S. Cl.
CPC .............. *H04N 19/00* (2013.01); *A61B 8/08* (2013.01); *B06B 1/00* (2013.01); *H03M 7/6005* (2013.01)

(58) Field of Classification Search
CPC .................................. A61B 8/08; B06B 1/00
See application file for complete search history.

(56) References Cited

U.S. PATENT DOCUMENTS

| | | | |
|---|---|---|---|
| 6,639,681 B1 * | 10/2003 | Magne | G01K 11/32 |
| | | | 374/E11.015 |
| 6,969,354 B1 | 11/2005 | Marian et al. | |
| 2016/0030000 A1 | 2/2016 | Sandhu et al. | |
| 2016/0058420 A1 | 3/2016 | Cinthio | |
| 2016/0220211 A1 | 8/2016 | Yamada | |

(Continued)

FOREIGN PATENT DOCUMENTS

| | | |
|---|---|---|
| CN | 109431606 A | 3/2019 |
| DE | 4436263 A1 | 4/1996 |

(Continued)

OTHER PUBLICATIONS

Guasch et al., Full-Waveform inversion imaging of the human Brain, NPJ, pp. 1-12 (2020).

(Continued)

*Primary Examiner* — Dixomara Vargas
(74) *Attorney, Agent, or Firm* — Hunton Andrews Kurth LLP

(57) ABSTRACT

The present application pertains to two-dimensional ultrasound transducers and systems, methods of making such transducers and systems, and methods for using such transducers and systems including processing of data acquired with such devices and systems.

16 Claims, 27 Drawing Sheets
(27 of 27 Drawing Sheet(s) Filed in Color)

(56) References Cited

U.S. PATENT DOCUMENTS

| | | | |
|---|---|---|---|
| 2016/0232655 A1 | 8/2016 | Lachner et al. | |
| 2017/0215846 A1* | 8/2017 | Sammoura | B06B 1/0666 |
| 2018/0264291 A1* | 9/2018 | Rem-Bronneberg | A61B 8/4488 |
| 2020/0007516 A1 | 1/2020 | Westin et al. | |
| 2020/0253587 A1 | 8/2020 | Barannyk et al. | |
| 2020/0349342 A1* | 11/2020 | Ralston | A61B 5/1176 |
| 2021/0069749 A1* | 3/2021 | Durocher | B06B 1/0685 |
| 2021/0215642 A1 | 7/2021 | Fincke et al. | |
| 2021/0407648 A1 | 12/2021 | Ravishankar | |
| 2022/0016673 A1* | 1/2022 | Lee | G06F 3/011 |
| 2023/0285000 A1* | 9/2023 | Williams | A61B 8/4488 |

FOREIGN PATENT DOCUMENTS

| | | |
|---|---|---|
| JP | 2010072765 A | 4/2010 |
| WO | 2012154335 A2 | 11/2012 |

OTHER PUBLICATIONS

International Search Report and Written opinion dated Oct. 19, 2023 issued in PCT/US2023/032622.

International Search Report and Written opinion dated Apr. 27, 2023 issued in PCT/US2023/017440.

Yeh, David T et al., Integration of 2D DMUT arrays with front-end electronics for ultrasound imaging, IEEE transactions on ultrasonics, ferroelectrics, and frequency control, vol. 55, No. 2, Feb. 2008, pp. 327-342.

Diarra, Bakary et al., Design of Optimal 2-D Nongrid Sparse Arrays for Medical Ultrasound, IEEE Transactions on Biomedical Engineering, pp. 3093-3102, vol. 60, No. 11, Nov. 2013.

Kim, Sumin et al., Efficient least-squares reverse time migration using local cross-correlation imaging condition, Journal of Geophysics and Engineering (2022) 19, pp. 376-388.

Chen, Weicen et al., Flexible Ultrasound Transducer with Embedded Optical Shape Sensing Fiber for Biomedical Imaging Applications, IEEE transactions on Biomedical Engineering, [From the Internet] www.ieee.org/publications/rights/index/html, 2023.

Zhou, Chenchen et al., Frequency-domain full-waveform inversion-based 2 musculoskeletal ultrasound computed tomography, J. Acoust. Soc. Am. 154 (1), pp. 1-18, Jul. 2023.

Willey, C.L. et al., An Element Localization Algorithm to Enable Flexible Ultrasound Array Imaging, [From the Internet] URL: https://www.afrl.af.mil/RX/ (A. T. Juhl), pp. 1-47, Mar. 2023.

Montero-Gato, Jon et al., Ultrasound of pneumothorax in neonates: Diagnostic value of the anterior transverse plane and of mirrored ribs, Pediatric Pulmonology. 2022;pp. 1-7.

Quinsac, Celine et al., Compressed Sensing of Ultrasound Images: Sampling of Spatial and Frequency Domains, IEEE, conference paper, pp. 1-7, Nov. 2010.

Hennenfent, Gilles et al., Random sampling: new insights into the reconstruction of coarsely-sampled wavefields, SEG/San Antonio 2007 Annual Meeting, pp. 2575-2579.

\* cited by examiner

FIG 1A: 2D circular probe with uniform distribution of elements according to Nyquist-Shannon sampling interval
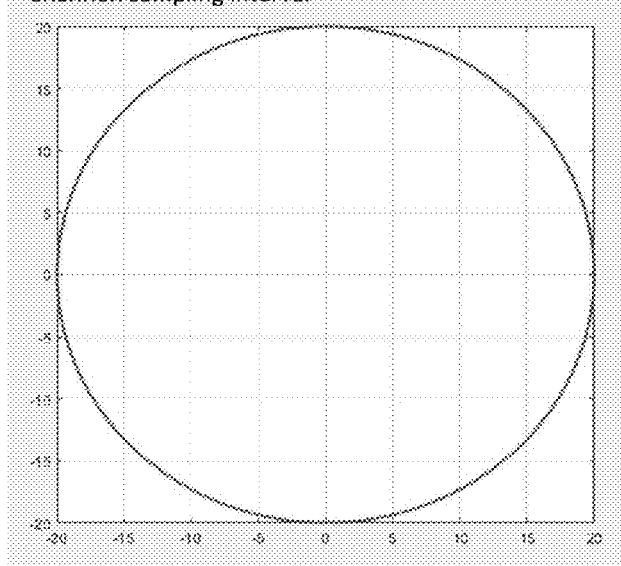
FIG 1B: 2D circular probe with uniform element distribution (zoom)
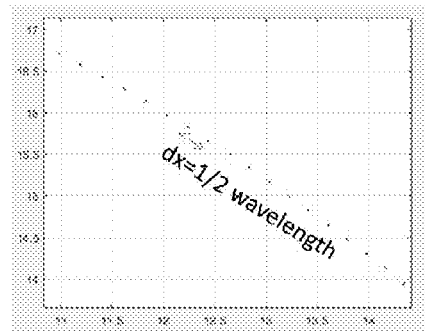

FIG 2: 2D optimized circular probe with random distribution of elements and reduced (sparce) number of elements
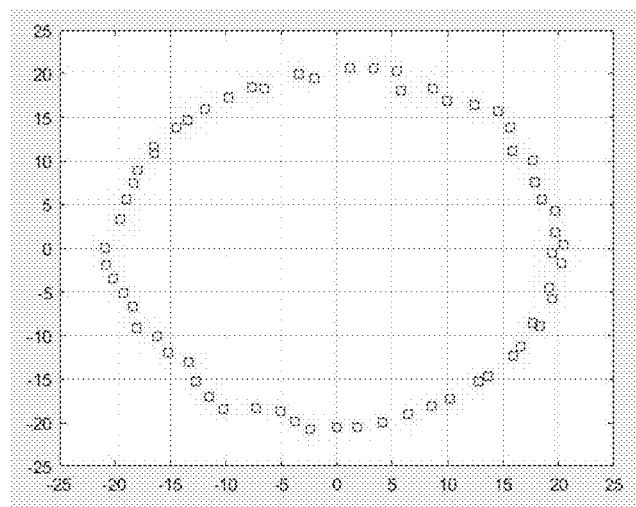

center point grid: uniform (a), staggered (b)

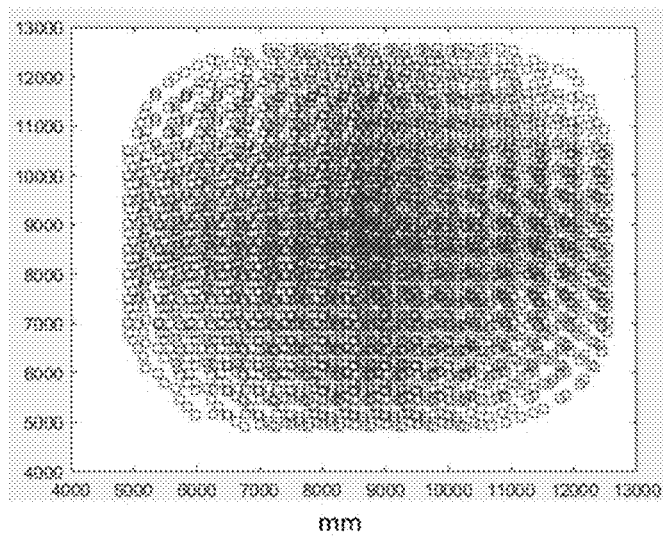
FIG 4: Element distribution for the 2D ultrasound probe with 3968 elements designed based on compressive sensing

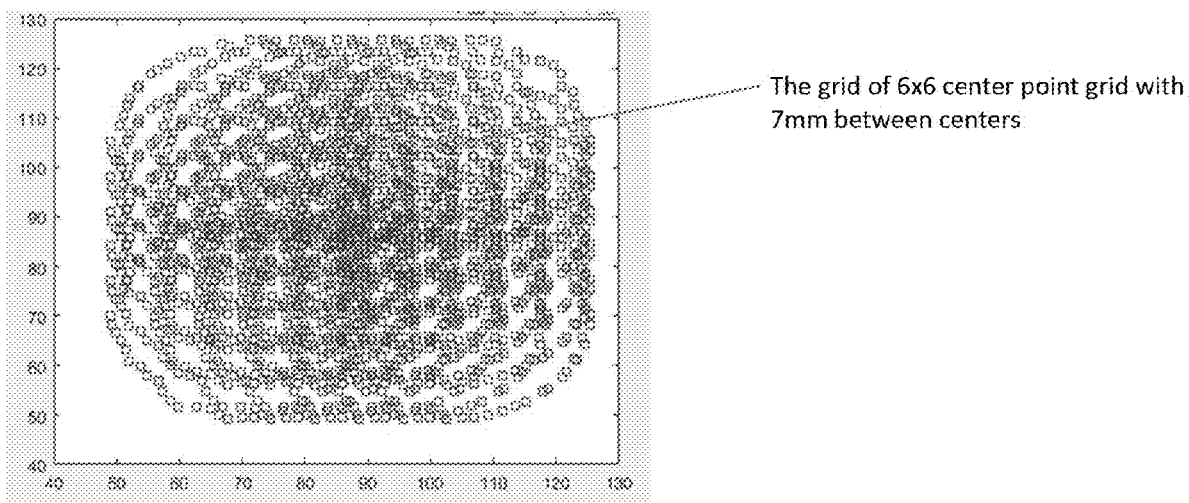
FIG 5: Element distribution for the 2D ultrasound probe with 2232 elements designed based on compressive sensing
The grid of 6x6 center point grid with 7mm between centers

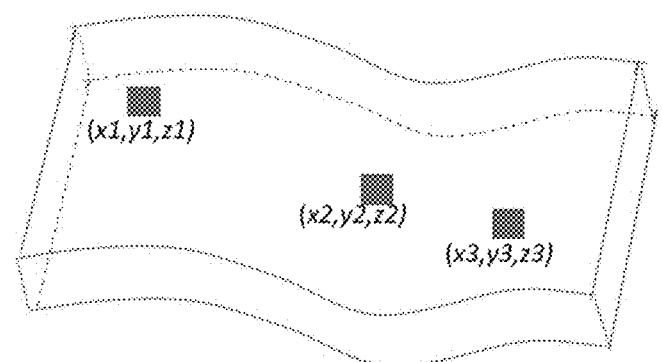
FIG 6: Flexible 2D ultrasound transducer requires to accurately know the (x,y,z) location of each element

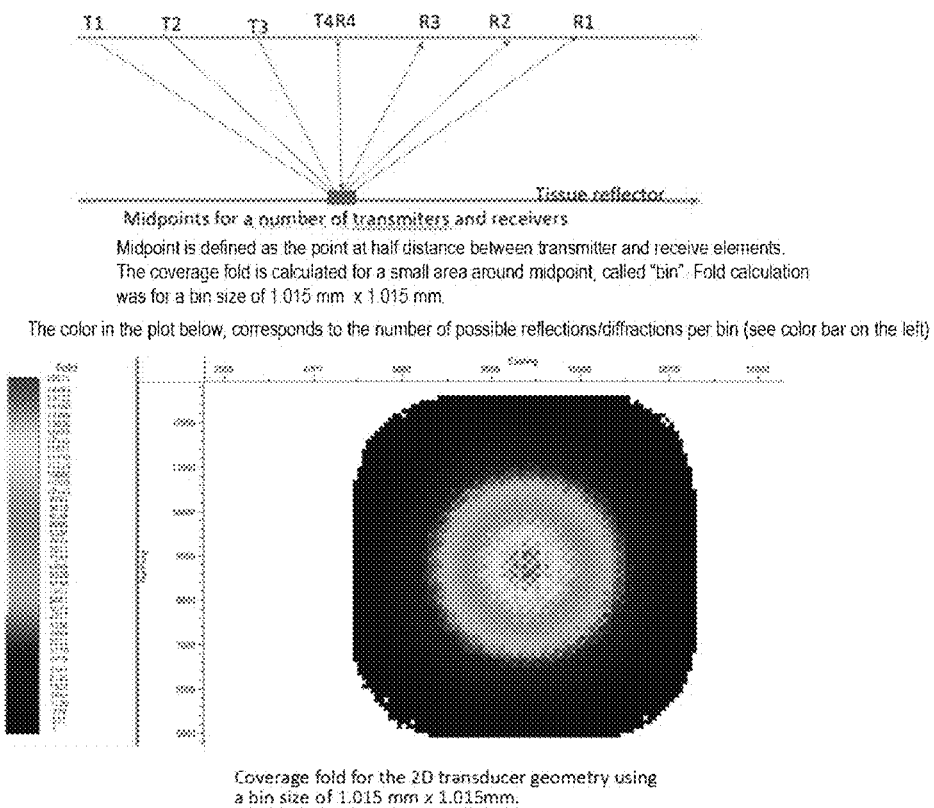
FIG 7: Coverage fold corresponding to the geometry of the 2D transducer FIG 8: Azimuth-offset coverage corresponding to the geometry of the 2D transducer
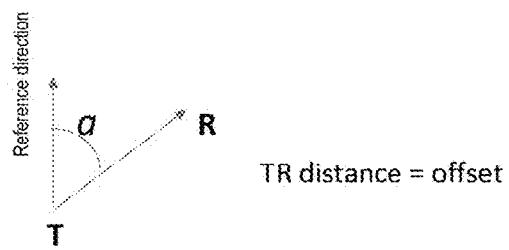
a = angle between a reference direction and direction defined by transmitter element (T) and receiver element (R); This angle is called azimuth angle.
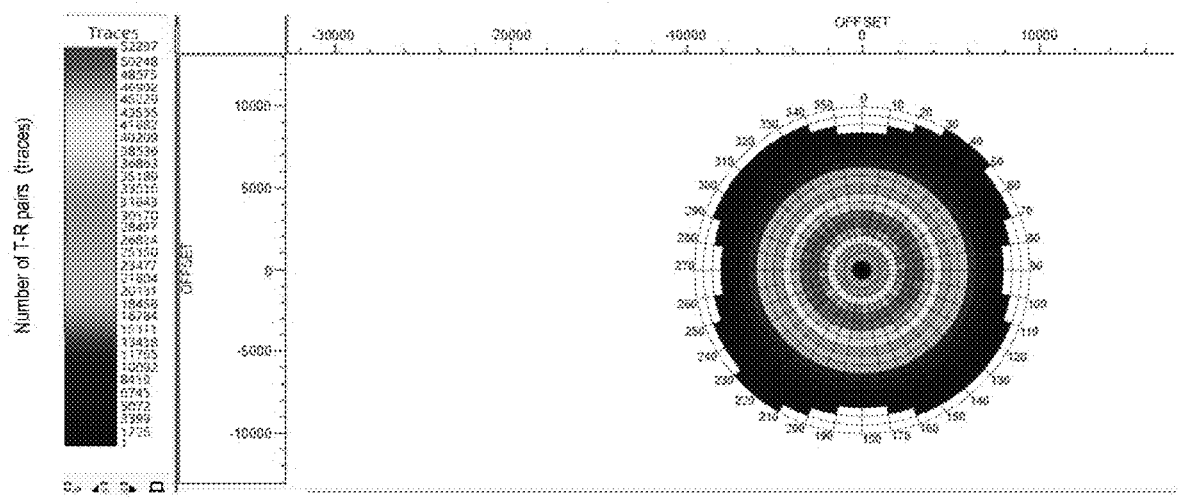

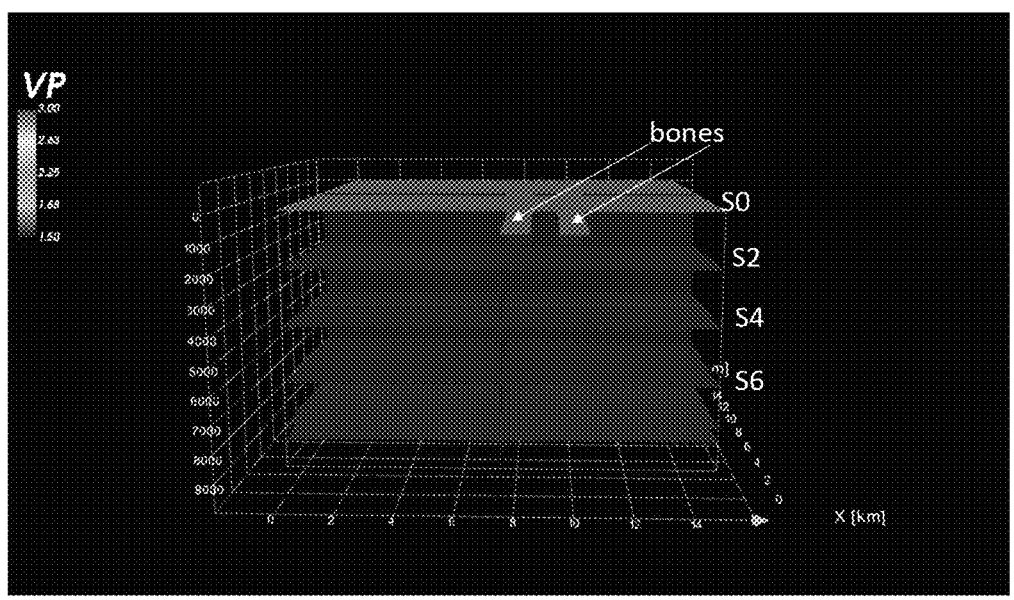
FIG 9A- Model with bones and flat tissues

FIG 9B- Model and the 2D elementary probe
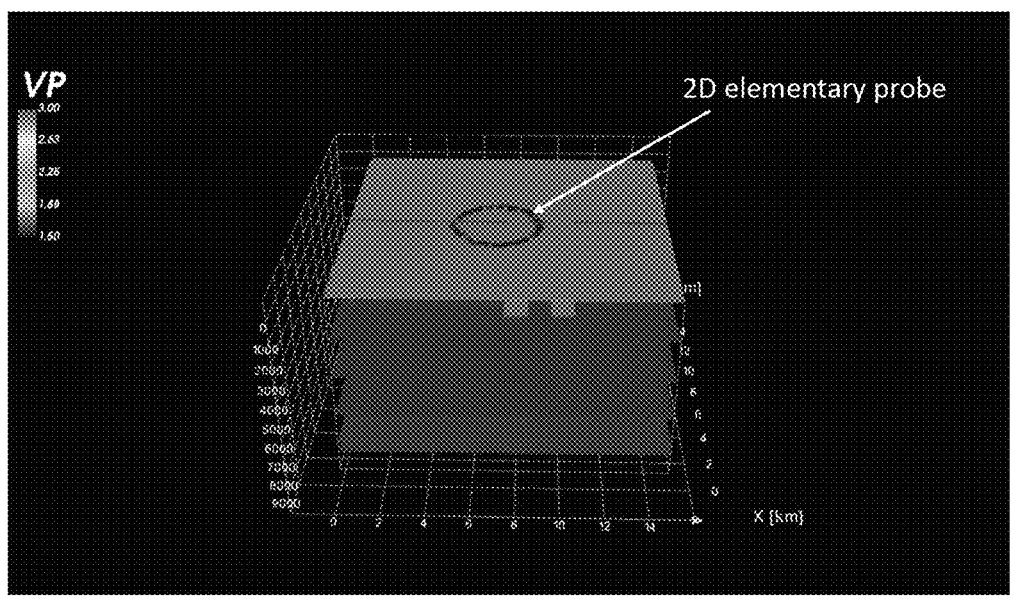

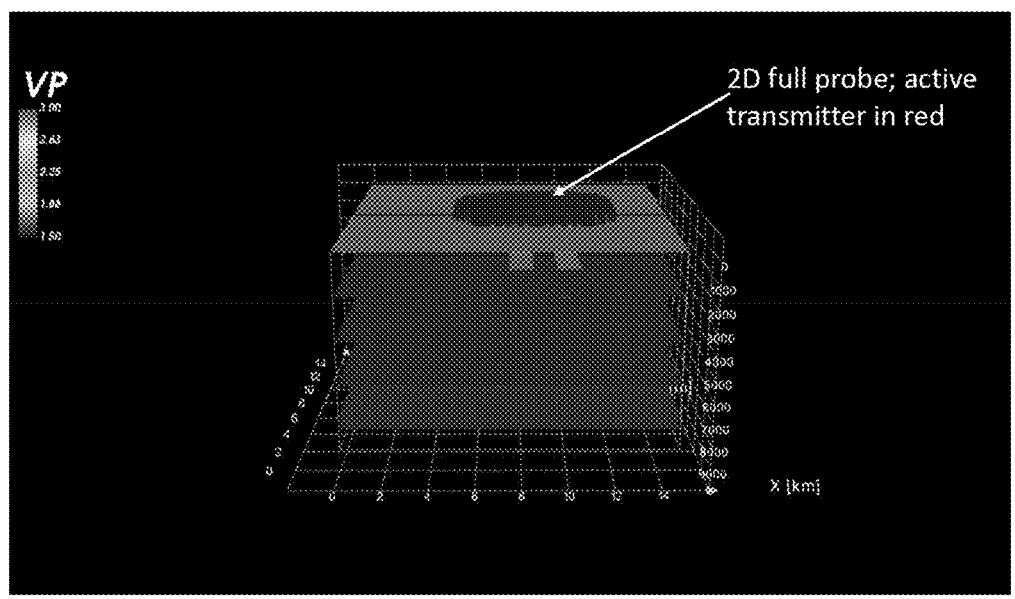
FIG 9C- Model and the 2D full probe

FIG 10: illumination of a deep tissue from the 2D elementary probe when a single transmitter is active
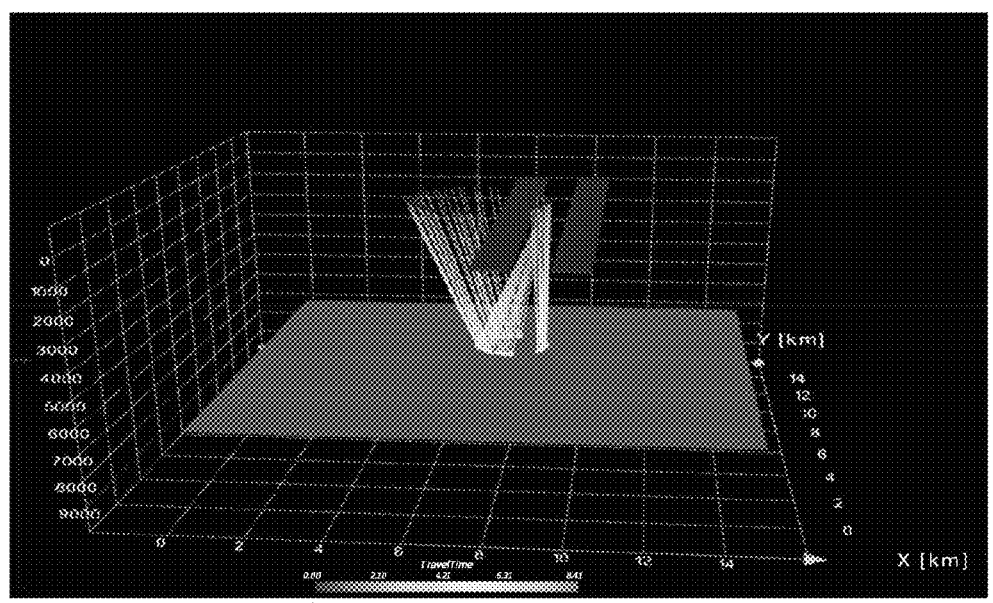

FIG 11: illumination of a deep tissue from the 2D full probe when a single transmitter is active
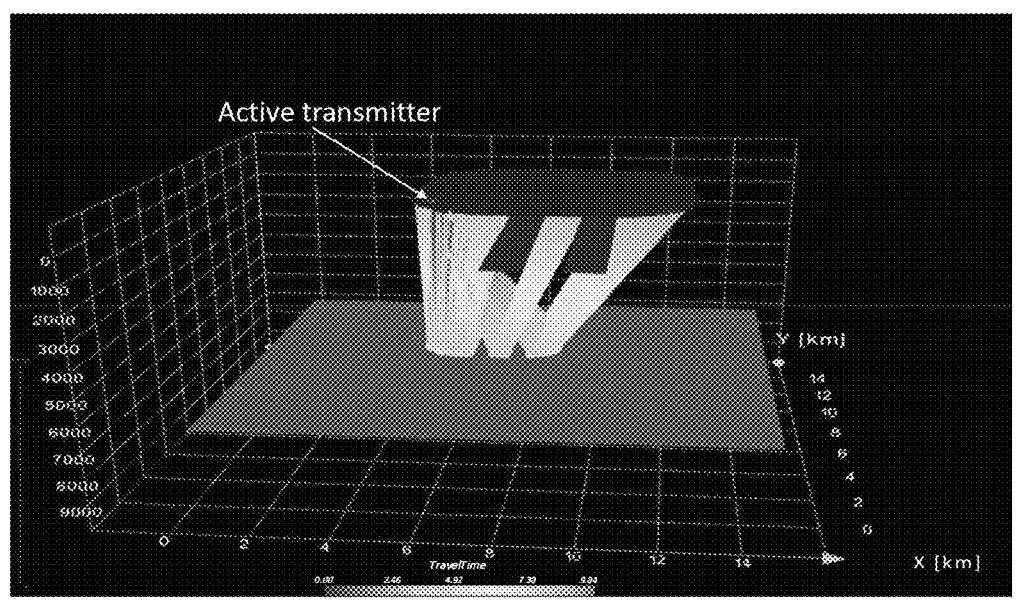

FIG 12: illumination of a deep tissue from the 2D full probe when a single transmitter is active (different transmitter location)
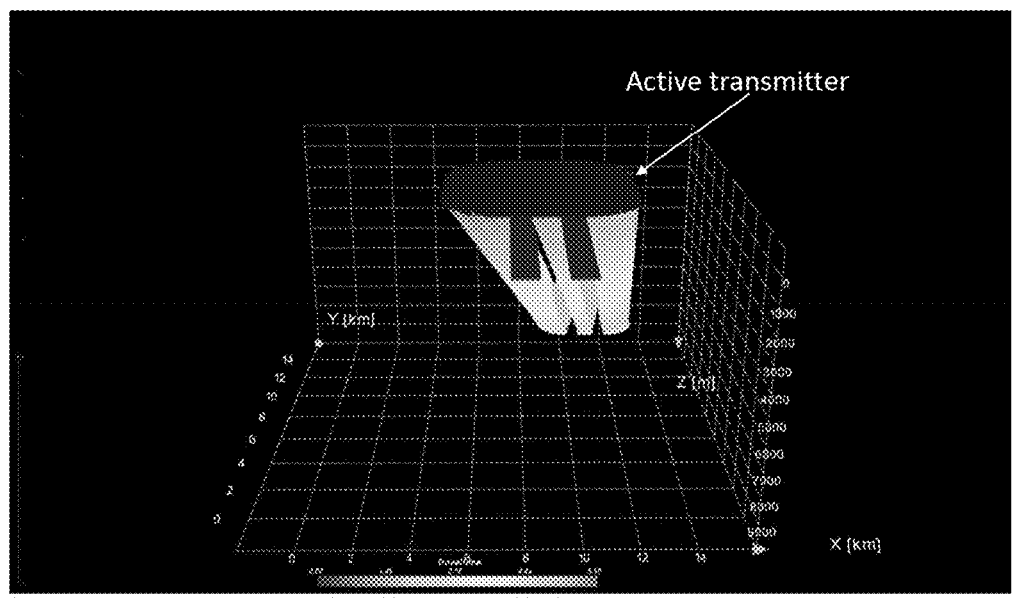

FIG 13: illumination of deep tissues from the 2D full probe when a single transmitter is activated
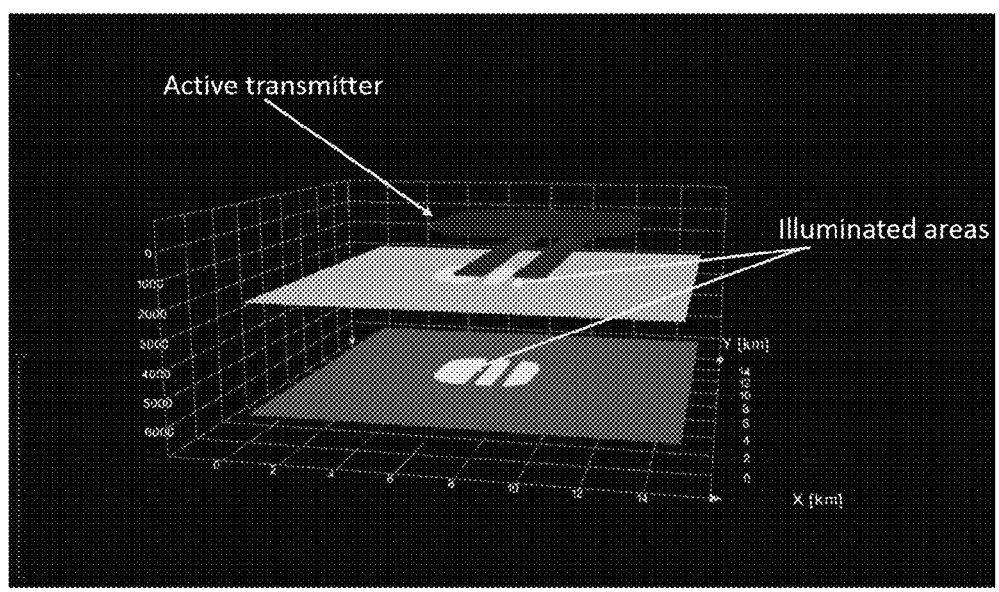

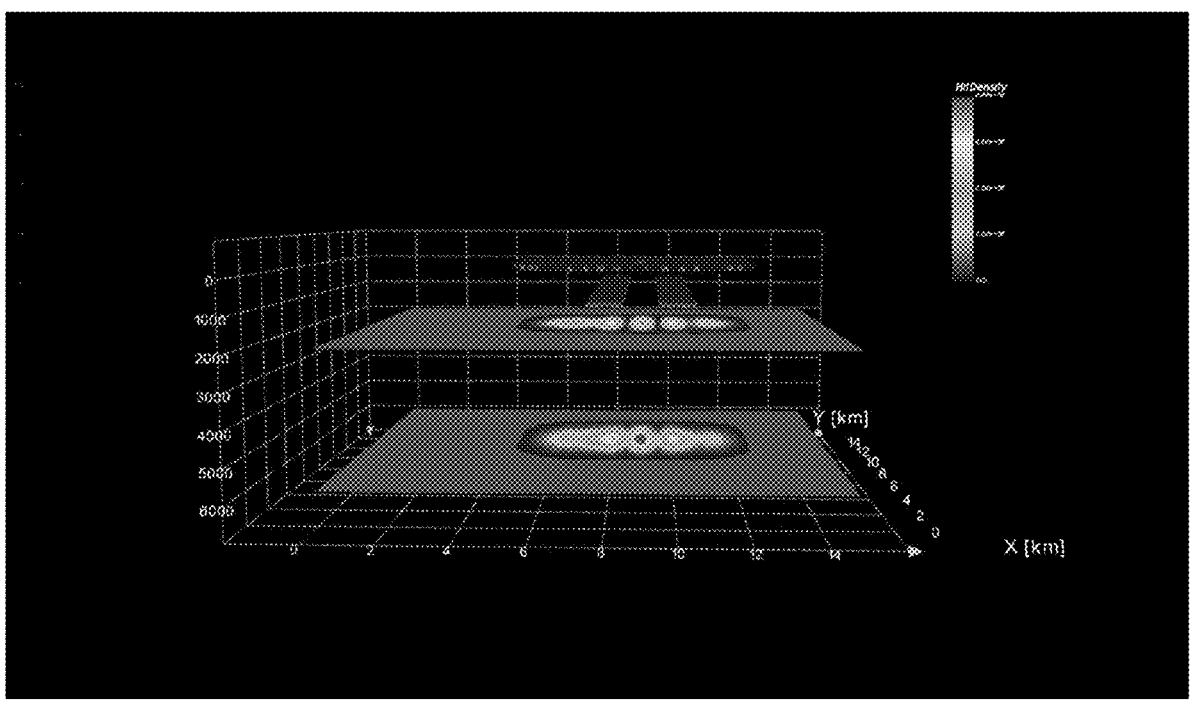
FIG 14: Illumination under the bones with primary reflections for flat tissues S2 and S6

FIG 15: Illumination of deep tissue (S6) from primary reflection
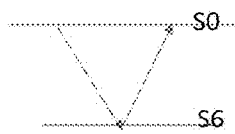
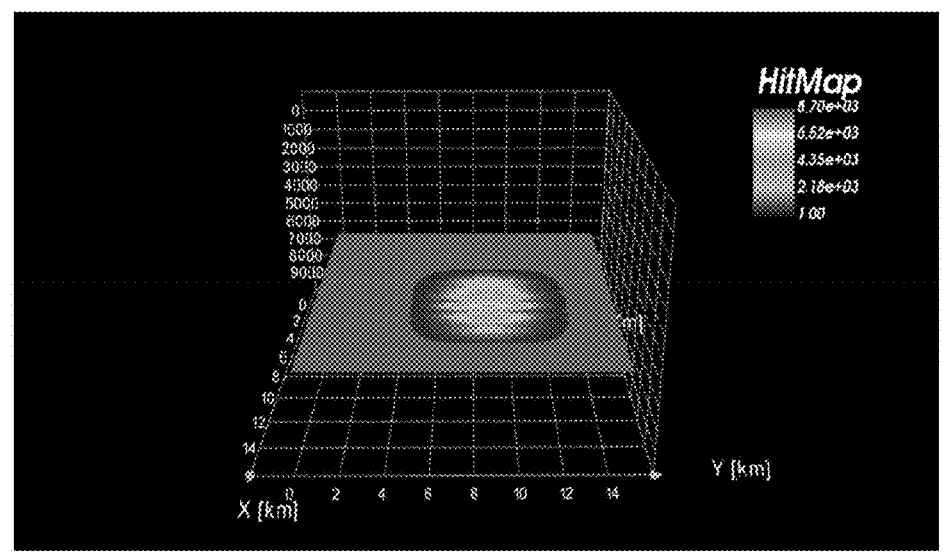

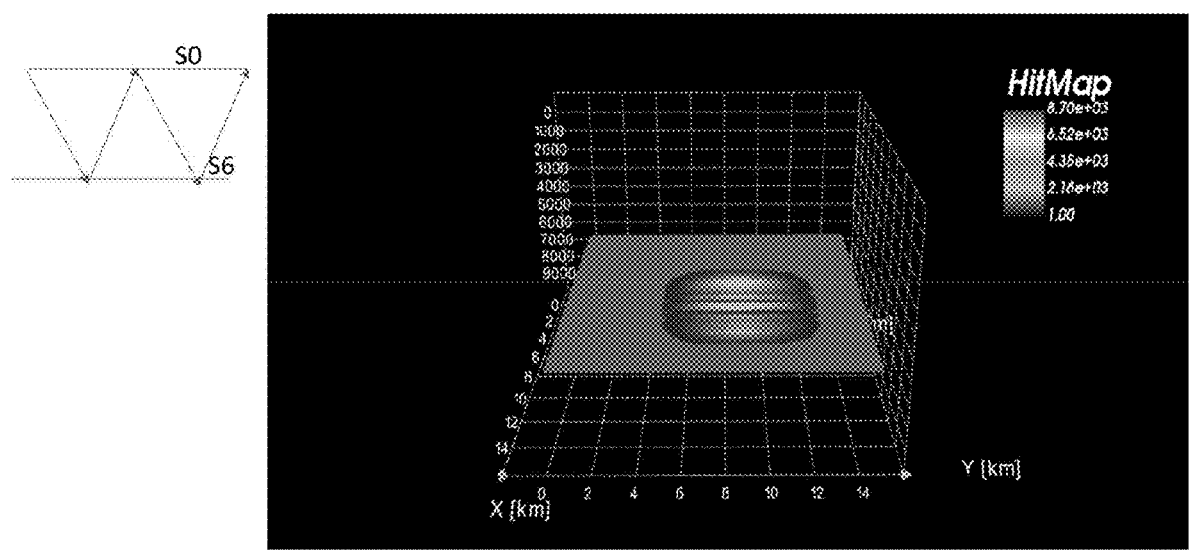
FIG 16: Illumination of deep tissue (S6) from a multiple reflection (S6S0S6)

FIG 17: Illumination of deep tissue (S6) from primary reflection (S6S0S6) and multiple reflection
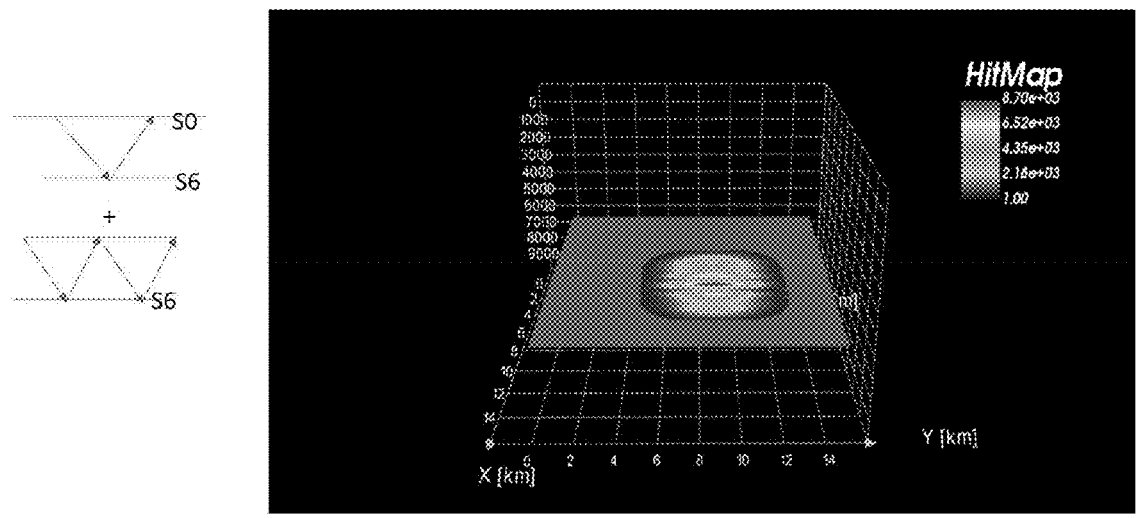

FIG 18: Illumination under the bones with multiple reflection (1 transmitter from 2D elementary probe)
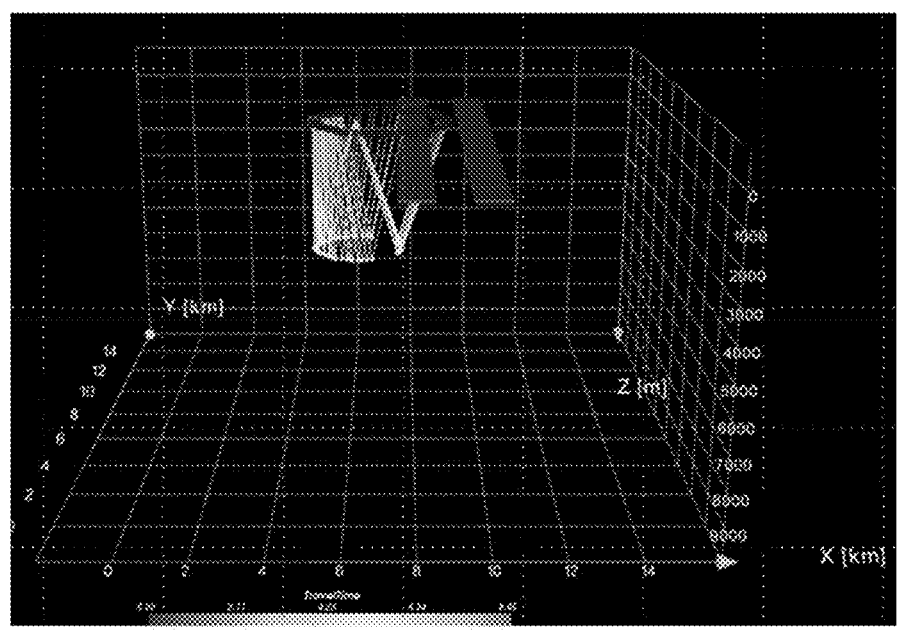

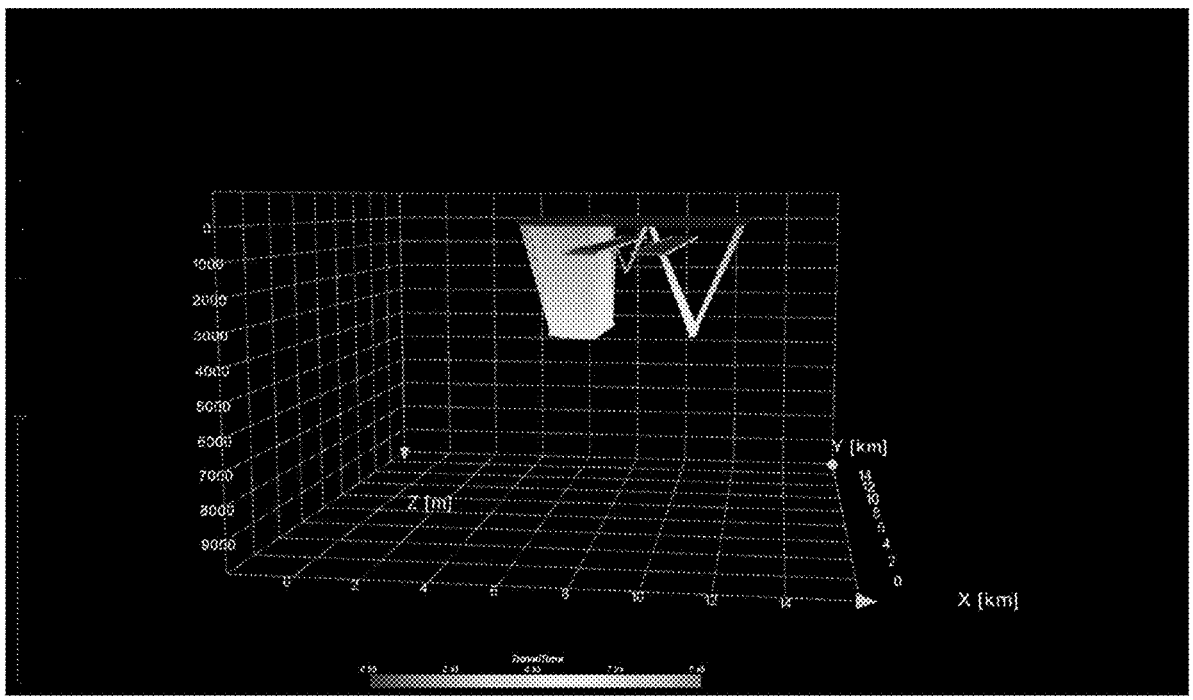
FIG 19: Illumination under the bones with multiple reflection (1 transmitter from full 2D probe is active)

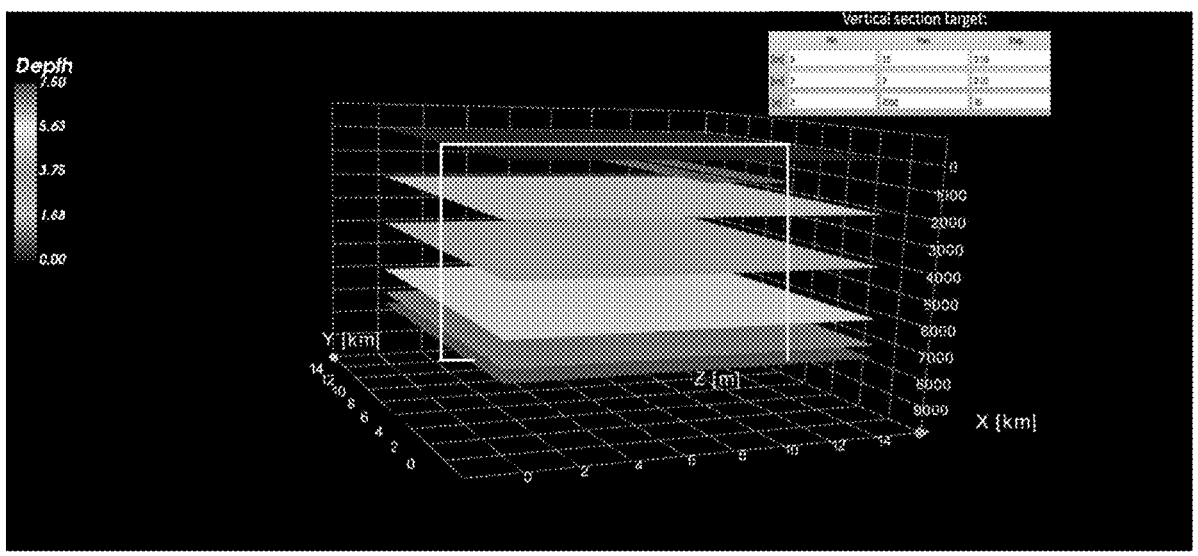
FIG 20A: vertical section in the model as target for the 3D migration

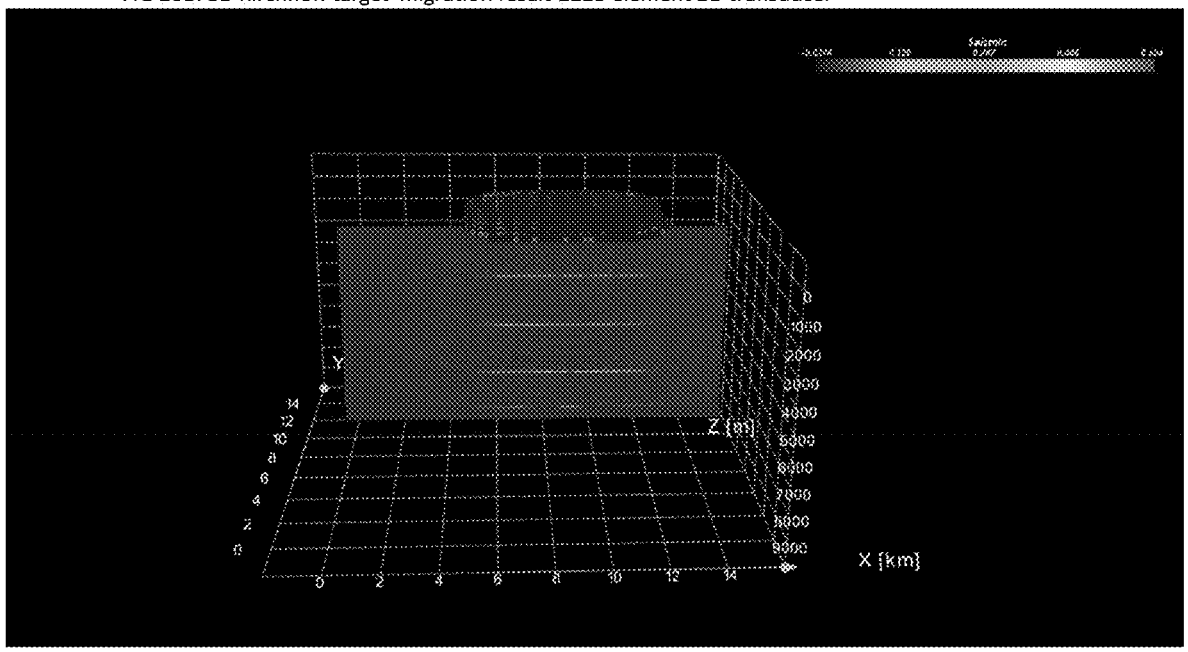
FIG 20B. 3D Kirchhoff target migration result-2223 element 2D transducer FIG 21A: Point spread function corresponding to the 2D transducer, background model and the scattering object
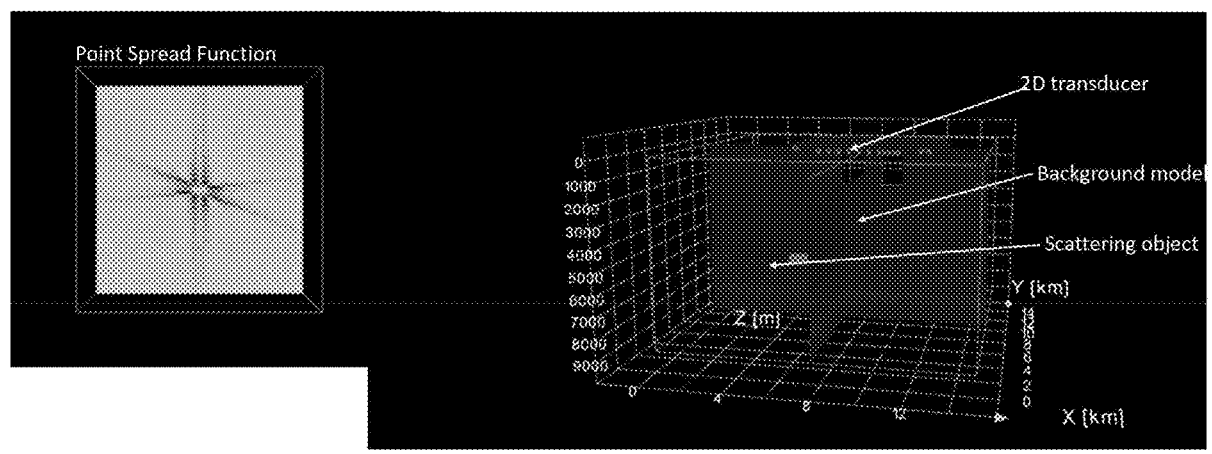

TWO-DIMENSIONAL ULTRA SOUND TRANSDUCERS AND SYSTEMS

CROSS-REFERENCE TO RELATED APPLICATIONS

For U.S. purposes this application claims priority to pending PCT application PCT/US23/17440 filed Apr. 4, 2023 which application claims priority to U.S. patent application Ser. No. 17/712,919, filed Apr. 4, 2022 (now U.S. Pat. No. 11,663,759), the content of which is incorporated in its entirety.

This application is also related to U.S. patent application Ser. No. 17/943,806, filed Sep. 13, 2022 (now U.S. Pat. No. 11,690,601) which application is incorporated herein by reference and is a continuation in part of Ser. No. 17/712,919.

This application also claims priority to pending U.S. patent application Ser. No. 17/993,699, filed Nov. 23, 2022, the contents of which are incorporated herein in their entirety.

FIELD OF THE DISCLOSURE

The present disclosure relates to two-dimensional ultrasound transducers and systems, methods of making such transducers and systems, and methods for using such transducers and systems including processing of data acquired with such devices and systems. A two-dimensional transducer (2D-transducer) generally has the elements placed in a 2D array (matrix array) whereas a one-dimensional transducers (1D-transducer) have elements placed along a single line.

BACKGROUND AND SUMMARY

Sonographic transducers are used in a variety of fields to generate images of hidden or inaccessible objects. For example, ultrasound transducers are used in the medical field to obtain images of tissues, organs, bones, and other biological material. Conventional transducers are handheld, probe-like devices that are pressed and moved around the subject until the desired image is generated. For instance, an ultrasound probe can be placed on a female patient's lower stomach to generate an image of the patient's uterus. To make an image that is generally clear and somewhat comprehensive, the probe must be moved around to many locations and in many directions against the patient. This is because human organs are 3D objects, while current ultrasound probes can only make 2D images or it only illuminate a small zones/slice of a large 3D organ. Accurate imaging of the human organs that are placed inside thoracic cavity, like heart and lungs, could be affected by the thoracic wall (rib cage and associated skin, muscle and fascia). It is difficult to get an accurate image of the organs and tissues placed inside the thoracic wall with a 1D transducer. If the ribs are ossified (adult patients), shadows will be generated behind the ribs that will mask the visualization of deeper tissues, if 1D transducers are used. If the ribs are not ossified, as is the case for the newborns patients, the ribs form anechoic structures and will produce strong echoes that will be reflected back from the surface and generate "mirror ribs". These "mirror ribs" are not accurately imaged with the 1D transducers and this could lead to false diagnostics (J. M Gato et al., 2022).

Another difficulty in ultrasound investigation may be the limited experience and training of the health professional handling the ultrasound transducer. Imaging behind the ribs with a limited size transducer is only possible if the transducer is placed between the ribs. To get usable images with 1D transducers often requires repeated movements over human body, and this process is time consuming and prone to error. These and other deficiencies exist. Therefore, there is a need to provide systems and methods that overcome these deficiencies.

Aspects of the disclosed embodiments include systems and methods to design and make a two-dimensional (2D) transducer, systems and methods to process the data acquired with the 2-D transducer, as well as systems and methods to produce three-dimensional imaged data and three-dimensional visualization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B shows a representative 2D circular transducer.

FIG. 2 shows the transformation of the 2D circular fully and uniformly sampled transducer from FIG. 1 into a 2D circular transducer that has a reduced number of elements (sparse array) that are randomly distributed, to comply with compressing sensing.

FIG. 4 shows element distribution for a representative 2D transducer.

FIG. 5 shows reducing the number of elements while preserving the same physical size of the 2D transducer by changing the number of points in the center grid and increasing the interval between centers.

FIG. 6 illustrates that building a transducer from flexible material better accommodates the human body.

FIG. 7 illustrates a density of the reflections/diffractions that could be generated from an elementary area ('bin").

FIG. 8 shows an azimuth-offset diagram corresponding to a 2D transducer.

FIG. 9A shows a 3D ray tracing using a model that consisted in flat surfaces and ribs to show the benefits of 2D transducer.

FIG. 9B shows a 3D ray tracing using a model that consisted in flat surfaces and ribs to show the benefits of 2D transducer.

FIG. 9C shows a 3D ray tracing using a model that consisted in flat surfaces and ribs to show the benefits of 2D transducer.

FIG. 10 shows illumination from elementary probe when a single transmitter is activated.

FIG. 11 shows illumination with full probe from a single transmitter using all receivers (elements).

FIG. 12 shows illumination with full probe from a single transmitter using all receivers (elements).

FIG. 13 shows illumination with full probe from a single transmitter using all receivers (elements).

FIG. 14 shows illumination of different tissues (surfaces) at different depths.

FIG. 15 shows benefits of using multiple reflections for improving signal to noise for the deeper tissues.

FIG. 16 shows benefits of using multiple reflections for improving signal to noise for the deeper tissues.

FIG. 17 shows benefits of using multiple reflections for improving signal to noise for the deeper tissues.

FIG. 18 shows benefits of using multiple reflections for illumination under the bones.

FIG. 19 shows benefits of using multiple reflections for illumination under the bones.

FIG. 20A shows target depth imaging using 3D Kirchhoff imaging algorithm wherein FIG. 20A represents the vertical section in the model used as target for the 3D Kirchhoff migration.

FIG. 20B represents the result of 3D Kirchhoff target migration.

FIG. 21A and FIG. 21B show point spread function generation using the 2D transducer geometry and an exemplary model described herein.

DETAILED DESCRIPTION

Figure 3A:
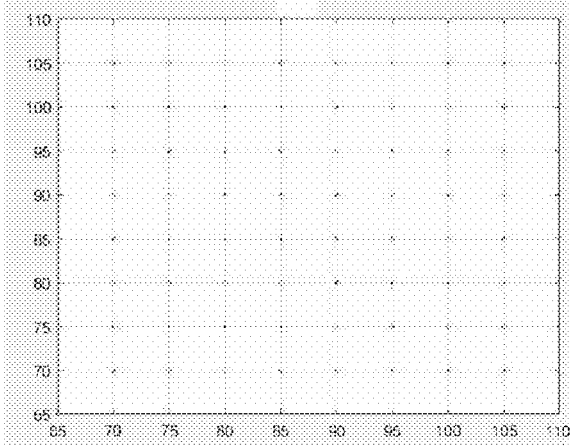
FIG. 3A shows a grid of center points that are uniform

The design parameters to consider for the 2D transducer array described herein include, for example, medical purposes of the 2D transducer, number of elements, the technology used for element fabrication, the size of the elements and of the 2D array, depth of penetration, required resolution, and/or the ability to generate data suitable for advanced imaging and inversion techniques.

The 2D medical ultrasound transducer described herein has one or more up to all of the features described herein. For example, the 2D transducer may be designed for imaging of heart, lung and/or tissues inside thoracic cavity, kidney and woman breasts. The 2D transducer also may be designed based on Capacitive Micromachined Ultrasonic Transducers (CMUT). The main advantages of CMUT technology over, for example, piezoelectric crystal technology for fabrication of elements include wide frequency response, smaller size elements, easier integration with the existing signal processing electronics, and/or better energy efficiency.

Advantageously, CMUTs are generally compatible with complimentary metal-oxide-semiconductor (CMOS) circuitry, allowing some signal processing elements to be located on the same chip as the transducer. For a large 2D transducer array CMUT technology may allow one to reduce the number of cables required to transmit the data. A representative way to accomplish this is to group the elements in sub-arrays; connect each sub-array to a dedicated chip electronics; apply gain control and beamforming.

The arrangement of the transducers in the form of array may advantageously be used for passive beamforming by controlling the phase and amplitude at each transducer. Active beamforming may be performed using digital signal processing. The output from sub-array electronics may be multiplexed into a smaller number of cables for transmission of data to the main system.

The 2D transducers described herein may be based on compressive sensing theory. If so, then one should consider ensuring a sparsity of the ultrasound signal in a certain domain and a random and sparse distribution of the elements. When both of these two requirements are fulfilled, then the full signal, properly sampled, can be properly reconstructed from the sparse representation with random distribution of elements. The aforementioned approaches may assist in ensuring optimized signal processing and enhancing imaging capability of the 2D transducers described herein.

2D Transducer Design Methodology

The methodology for determining the locations of random elements, the number of elements in the 2D transducer and the element size may vary depending upon the type of transducer, elements employed, and desired results. In some embodiments the methodology may be based on one or more up to all of the following four steps which may be accomplished with, for example, an integrated software program. While representative specific numbers are described below, it should be appreciated that these are for illustration purposes only and are not limiting.

(1) Design Transducer Design a 2D circular transducer with a radius R of a minimum of about 20 mm for a device with the capability to image under the rib. The elements are distributed in a substantially uniform manner along the circle circumference using, for example, a Nyquist-Shannon sampling interval. For a maximum frequency of 3 MHz and a velocity of sound propagation of 1540 m/s, the nominal sampling interval may be 0.2567 mm. The 2D probe with a circular distribution of elements will typically allow one to image the organs and tissues from all angles, 0 to 360 degrees ("full-azimuth"). A drawing of this representative 2D circular transducer is presented in FIG. 1.

(2) Optimize element distribution: The 2D circular fully and uniformly sampled transducer (from step-1) is transformed into a 2D circular transducer that has a reduced number of elements (sparse array) that are randomly distributed, to comply with compressing sensing (FIG. 2). An optimization algorithm, such as a genetic algorithm or simulated annealing algorithm such as those described by Diarra et. al, 2013 may be used to determine the optimum (x,y) locations of the elements. If desired various cost functions could be used for the optimization algorithm. For example, one may wish to reduce or minimize the difference in the beam patterns between the fully sampled, uniformly distributed elements transducer and sparse-sampled and randomly distributed elements transducer, in terms of the main lobe size and the ratio between main lobe and the side lobes. A cost function may be employed proposed for the optimization algorithm to maximize the spectral gap associated with the matrix, M, defined by the element locations. Such a function has been described by, for example, Lopez et al. The rows and columns in matrix M where an element exist are populated with "1" and the rest of the rows and columns are populated with zeros. The spectral gap is usually defined as the ratio between the first and second singular values of matrix M. If the spectral gap is large this often means that signal recovery via low-rank minimization method will be successful from measurements that are sparse and randomly distributed. This 2D optimized circular transducer with random elements (FIG. 2) is used to generate the full size 2D transducer with random distribution and with the desired dimensions, for example 75 mm×75 mm. This 2D optimized transducer with random elements may be referred to as a 2D elementary probe.

Figure 3B:
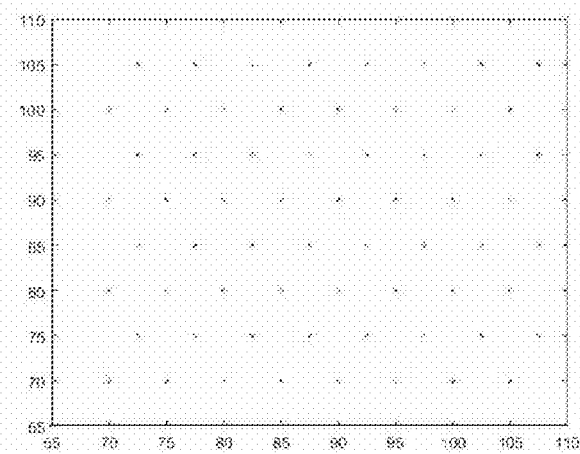
FIG. 3B shows a grid of center points that are staggered.

(3) Grid Point Generation Next, a grid of points is generated that represent the centers for the 2D elementary probe. The (x,y) locations of the centers, and the separation between centers, are defined based on the desired size of the 2D transducer. The grid of center points could be uniform (FIG. 3A) or staggered (FIG. 3B).

(4) Probe Placement Next, the approximate center of the 2D elementary probe is placed in each grid point center. Each time the 2D elementary probe is placed in a grid point center, it is verified via software or other convenient manner that the new elements are separated by a minimum ½ wavelength from the previous elements. The separation between elements of ½ wavelength takes into account the size of the transducer elements that is typically ½ wavelength.

The results of the four steps described above typically give the (x,y) random locations of elements for the 2D transducer. The element distribution for the final 2D transducer is shown in FIG. 4. This representative transducer has 3968 elements based on the parameters that were used in this design example: circle radius=20 mm, number of randomly distributed elements for the optimized elementary 2D probe=62, number of center points in the grid=64. The parameters that determine the size of the 2D transducer are circle radius and center point grid parameters. For example, an 8×8-point grid with 5 mm between grid points and a radius R=20 mm provides an array with a size of 75 mm×75 mm.

The transducer design can be readily changed to define a probe with a different number of elements or a different size. Generally, there are two parameters to change: the number of centers for the 2D elementary probe and the interval between centers. For instance, if one wants to reduce the number of elements but still wants to preserve substantially the same physical size of the final 2D transducer, one changes the number of points in the center grid to 36 (6×6) and increases the interval between centers to 7 mm (FIG. 5).

In some embodiments the size of the elements (CMUT) may be designed to be variable across the 2D transducer, e.g., smaller elements may be in the center of the array and larger elements may be toward the edges. This type of distribution may offer one or more up to all of the following benefits: (1) better resolution near the center of the imaging field due to higher frequency produced by smaller elements; (2) better penetration and/or a wider view towards the edges due to a lower frequency associated with larger elements; and/or (3) adaptive focusing and/or beamforming. The calculation of the element size as a function of distance of the element from the center of the probe may be determined based on an optimization algorithm considering both the vertical and the horizontal resolution in the cost function.

In some embodiments all or substantially all of the elements of the composite 2D transducer may be independently activated as a transmitter and receiver. By controlling the timing and phase of the ultrasound signal emitted by each element, the ultrasound waves may be focused and/or steered in a particular direction and/or to a certain depth. This process, known as beamforming, may advantageously be performed during both transmission and reception. With a large number of elements randomly distributed over a larger surface, novel beamforming techniques may be employed such that multiple parts of the tissue or human organs can be imaged simultaneously. This potentially results in improved resolution, improved signal-to-noise ratio, and/or reduced acquisition time. A machine learning algorithm may be implemented to evaluate the effective phased arrays for different applications and/or the types of beamforming that may be generated.

Flexible transducer construction: While the material(s) of the transducer may vary depending upon the application in some embodiments the transducer is built from a flexible material to better accommodate the human body, such as the chest or woman breast (FIG. 6). A flexible 2D transducer assures very good coupling with the human body and a uniform pressure distribution. The amount of gel that is typically used is reduced. This will maximize the transmitted and received ultrasound energy and could also reduce patient discomfort and potential motion artifacts. A good coupling between transducer elements and human body could cause the relative locations of the transducer element to change. Accurate imaging and inversion of ultrasound data requires knowing the exact locations of transducer elements.

There are at least two ways that may be used to determine accurately the locations of the elements: (1) use of the traveltimes from the direct wavepaths between transmitting elements and receiving elements, to determine the element locations as described by Willey A. et al, 2023 and/or (2) use of fiber optic shape sensing technique to determine the exact locations of the elements as described by Chen W. et al., IEEE transactions, 2023. While the transducers described herein may be designed to use either way, it is believed that the use of travel times may simplify the manufacturing process while allowing it to be fully integrated in the 3D imaging-inversion process.

Using CMUT for the fabrication of flexible 2D transducers is advantageous as the CMUT elements may be made thinner and more conformable with human body for an improved contact with the skin over conventional transducers.

As mentioned previously, the signal-to-noise ratio of data acquired with the 2D transducer having a large number of elements (transmitters and receivers) is increased over conventional transducers. This is due at least in part to a very high density of reflections/diffractions (scattered waves) generated from human tissues or organs. To illustrate this, the midpoint coverage fold corresponding to the geometry of the 2D transducer was calculated for a flat tissue reflector assuming constant sound velocity propagation above the tissue. This is presented and explained in FIG. 7 which illustrates the density of the reflections/diffractions that could be generated from an elementary area ('bin") of 1.015 mm×1.015 mm. The very high number of reflections/diffraction (scattered waves) could translate, after processing, into images with a high signal-to-noise ratio.

Advantageously, the illumination of the internal human organs and tissues is from all azimuths and from different offset ranges. Placing the 2D optimized circular transducer in different center points across the surface of the 2D array ensures illumination from 0 to 360 degrees and signal penetration inside thoracic cavity or abdomen. The azimuth-offset diagram corresponding to this representative 2D transducer is shown in FIG. 8. The 'full azimuth" type illumination is beneficial for imaging under the bones and for imaging of internal organs like heart, lung, liver, woman breast, etc. Full-azimuth illumination allows more accurate diagnostics based on advanced 3D type inversion and imaging algorithms and data visualization. Other benefits of full-azimuth illumination could be (1) improved signal-to-noise ratio, as the noise acquired from different directions could be incoherent and it will be easy to remove; and/or (2) reduced acquisition time as it is not necessary to substantially change or even move the transducer location to be able to image the organ from a different angle; and/or (3) improved attenuation of multiple reflections and reverberations during imaging due to the full-azimuth illumination. If desired, the multiple reflections could be considered signals and thereby used in the images to provide additional information.

The transmitter-receiver separation (offset) corresponding to a large probe, full-azimuth distribution and the wide band enabled by CMUT will allow the use of full-waveform inversion for deriving a more detailed velocity model and very accurate imaging of the human organs and tissues, taking advantage of the entire recorded wavefield: reflections, diffractions, and multiples (including reverberations).

Examples

To further demonstrate the benefits of the instant 2D transducers a 3D ray tracing was performed using a model that consisted in flat surfaces and ribs (FIG. 9A, 9B, 9C). The spatial dimensions of the model and of the 2D transducer with random elements were scaled by a factor of 100,000. The model included flat tissues placed at 2000 m (20 mm), 4000 m (40 mm), 6000 m (60 mm), 7000 m (70 mm) and the bones at 700 m (7 mm), with a width of 1000 m (10 mm) and a thickness of 200 m (2 mm). Note: the width of the bones (ribs) was exaggerated to demonstrate the capability of the 2D transducer to image under the bones. The velocity of the sound in tissue was 1520 m/s to 1560 m/s and the velocity of the sound in bones were 3000 m/s. The density in the model was kept constant (derived from velocities based on Gardner equation). Ray tracing is an attractive option to simulate medical ultrasound experiments where very high frequencies are considered, because the frequency is not a specific parameter in simulation.

An objective of the performed simulation was to illustrate the capabilities of the 2D array geometry (element distribution) for illumination of the human tissues, without applying beamforming. The following simulations were performed to demonstrate illumination capabilities:

Illumination from the elementary probe when a single transmitter is activated (FIG. 10)

Illumination with the full probe from a single transmitter and using all receivers (elements) (FIG. 11, 12, 13)

Illumination of different tissues (surfaces) at different depths (FIG. 14)

Benefits of using multiple reflections for improving signal to noise for the deeper tissues (FIGS. 15, 16, 17)

Benefits of using multiple reflections for illumination under the bones (FIG. 18,19)

Target depth imaging using 3D Kirchhoff imaging algorithm (J. Etgen, SEG 2012): FIG. 20A represents the vertical section in the model used as target for the 3D Kirchhoff migration while FIG. 20B represents the result of 3D Kirchhoff target migration.

Figure 21B:
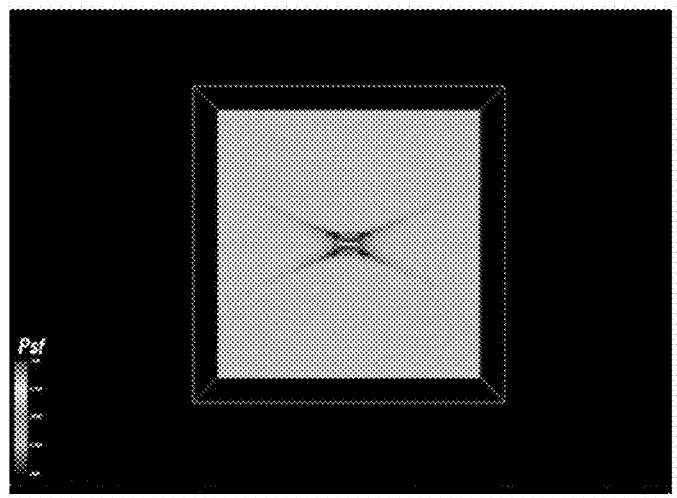
Figure 22A:
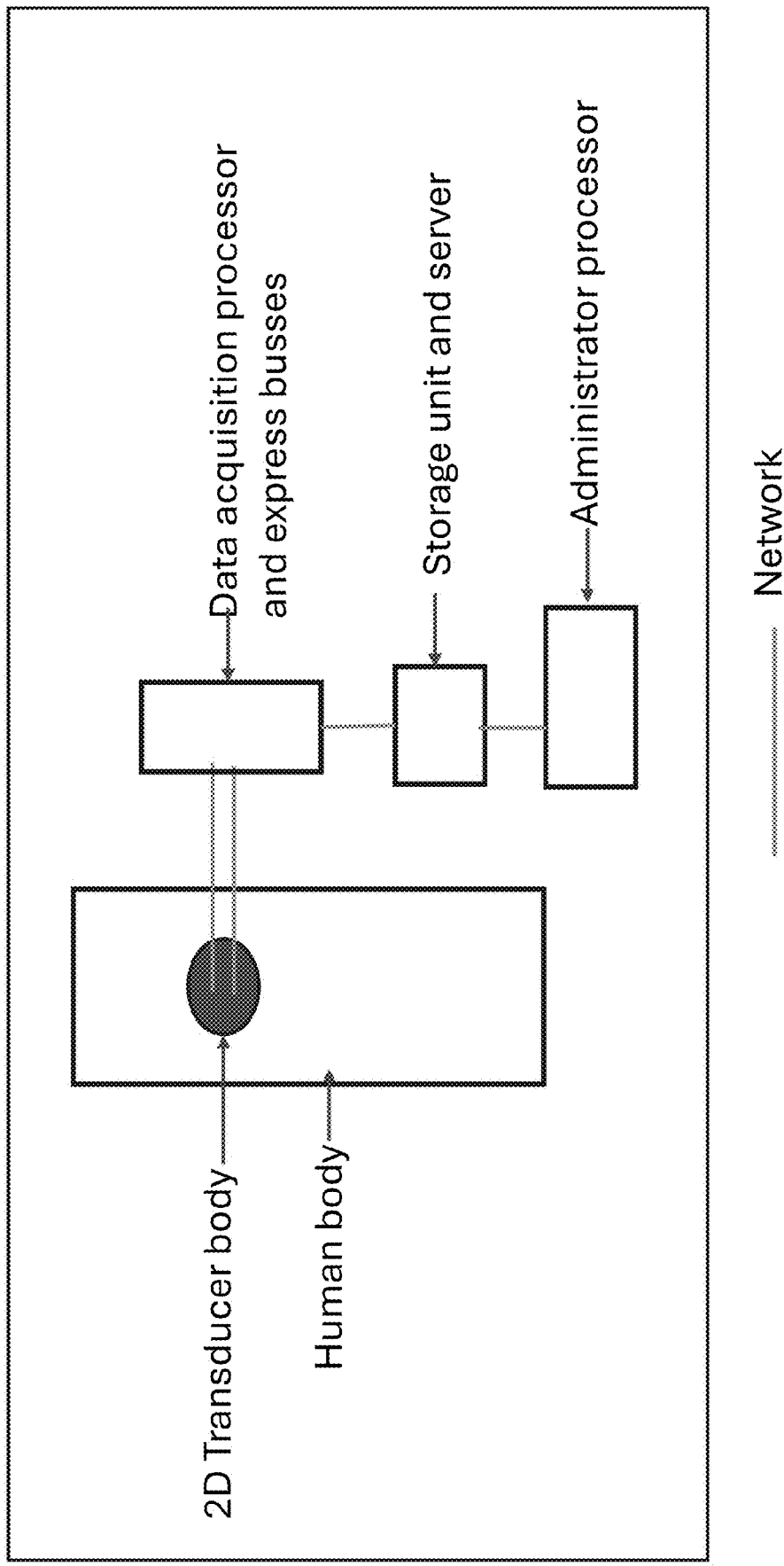
FIG. 22a shows a block diagram of a human body, 2D transducer body, data acquisition processor, express busses, storage unit, administrator processor, server, and network.
Figure 22B:
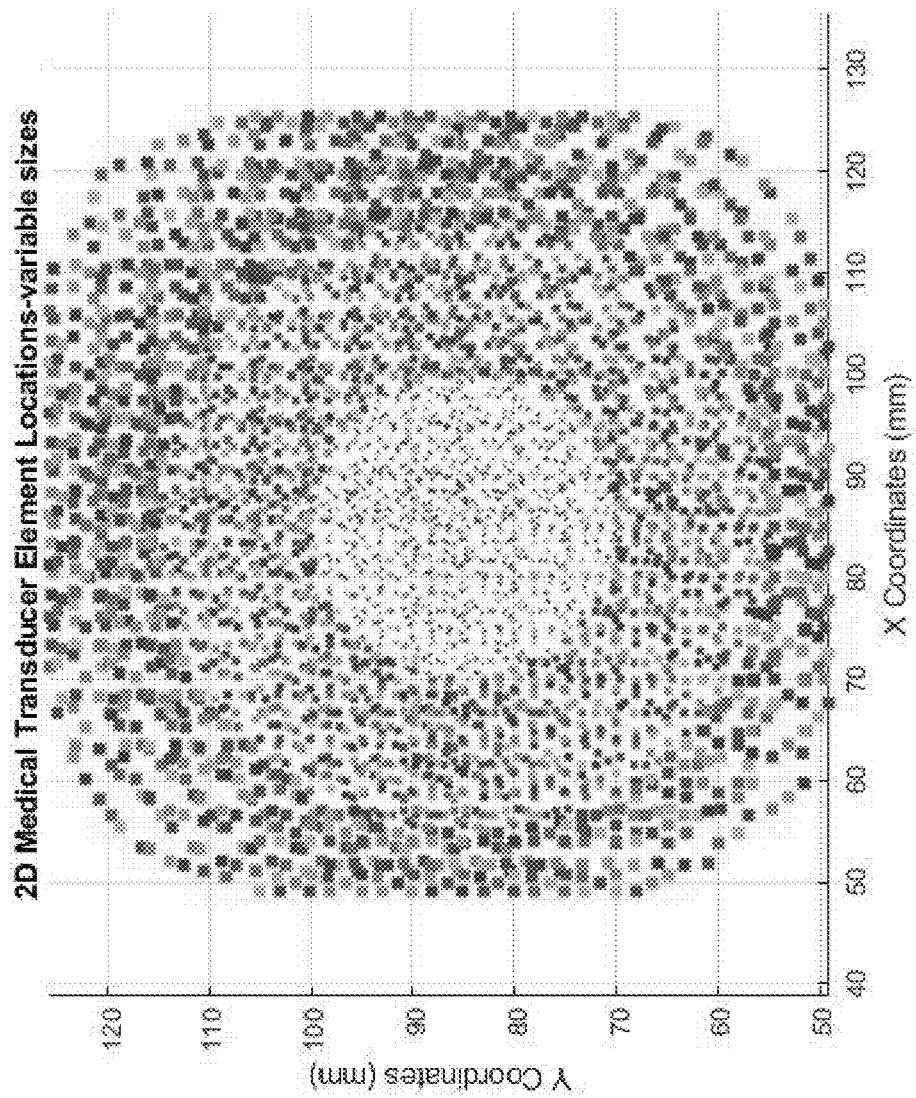
FIG. 22b shows an expanded view of FIG. 22a's 2D medical transducer body with micromachined ultrasound transducer elements larger in size near an edge of the two-dimensional ultrasound transducer.

Point spread function generation using the 2D transducer geometry and the described model (FIG. 21 PART 1 and PART 2).

The simulations described above showed the following:
the 2D transducer can image the tissues under the bones without performing beamforming due to full-azimuth, larger transmitter-receiver distances, and high density data resulting from collecting ultrasound medical data with the 2D transducer;
multiple reflections could be imaged to enhance the signal/noise of the deeper tissues, providing additional information to imaging with primaries;
advanced 3D imaging algorithms, like 3D Kirchhoff migration, could be successfully used to image the data acquired with a 2D transducer; Imaging of the data was done without reconstructing (interpolating) the data to dense sampling prior to imaging, as it is required by compressing sensing. Performing wavefield reconstruction (interpolation) prior to imaging will further improve the results.

Point spread function generated from a point located on scattering object shows a high spatial resolution in both, X and Y directions.

The data processing and imaging for the 2D transducer with many elements could be performed in a number of ways. In one representative method the processing and imaging is performed in in two steps. First, one may apply typical medical ultrasound processing based on phased array and beamforming. The known beamforming techniques that could be applied include, for example, delay-and-sum, dynamic receive focusing, synthetic aperture beamforming, and/or adaptive beamforming. This type of processing will be performed locally or on the 'local cloud system'. A configuration for this 'local cloud system' could include multiple CPUs and GPUs (Graphic Processing Unit), large and fast accessible memory, and high-speed communication capability. The results of this processing-imaging step could be presented as 2D images or 3D images. Second, one may apply advanced inversion and imaging techniques that are enabled by the 2D transducer data acquired with full-azimuth, long offsets, high density, and very good low and high frequencies due to CMUT technology. The inversion-imaging method based on wave equation propagation like full waveform inversion as described by Yu et al., 2023 and/or least square reverse time migration as described by S. Kim et al., 2022 could be used for imaging of ultrasound data. Performing the advanced 3D inversion-imaging for 2D ultrasound data may involve transferring the data via high-speed buses to a cloud computing system as described in, for example, U.S. Pat. Nos. 11,663,759; 11, 690,601; and pending U.S. patent application Ser. No. 17/993,699. Ultrasound data that is acquired based on compressive sensing requires that the data first be reconstructed (interpolated) to a dense wavefield and then imaged. In some embodiments, the two steps may be combined to produce the final 3D image thereby reducing the total processing time.

Representative Embodiments

1. A two-dimensional ultrasound transducer, wherein the transducer comprises: a two-dimensional body; and a plurality of Capacity Micromachined Ultrasound Transducers distributed across the two-dimensional body, wherein each element is capable of transmitting and receiving a plurality of sound waves.

2. CMUT allows one to reduce the number of cables for data transmission from the acquisition system to the local processing system or to the cloud processing system via network by grouping the CMUTs into array and integrating the arrays with existent chip electronics for multiplexing and other signal processing.

3. Method to generate from a 2D circular transducer with a radius R, larger than the average size of the human ribs, that has a number of elements that are uniformly distributed with a sampling interval equal with ½ wavelength, an optimized 2D circular transducer with random distribution of elements and a reduced number of elements (sparse distribution) using an optimization algorithm. The result is the 2D circular optimized transducer or 2D elementary probe.

4. The radius of the 2D circular transducer is defined to be larger than the average size of the human ribs.

5. Use of the spectral gap as a cost function for the optimization algorithm.

6. Method to determine the (x,y) randomized element location of the 2D transducer by associating the 2D elementary probe to the grid of center points. The center point grid could be uniform or staggered. The software used in design will provide a table containing the following information: 1) element number; 2) (x,y,z) location; 3) distance from the center of the probe location (X0,Y0,Z0) to the element; 4) size of the element as a function to distance to (X0,Y0,Z0). This table could be used for manufacturing and for ultrasound data simulations.

7. The 2D CMUT transducer is built from flexible material to allow perfect coupling with the human body. The determination of (x,y,z) coordinates of each element after coupling is part of the 3D inversion-imaging algorithm and is based on the transmitter-receiver travel time measurements.

8. Method to improve the resolution and penetration of the 2D transducer by using variable dimensions for the CMUT-elements: smaller dimension in the middle of the array and higher dimension towards the edges.

The flexible 2D transducer assures uniform pressure distribution and maximizes the ultrasound energy that is transmitted and received because of perfect coupling and reduced amount of gel.

9. Method to improve the signal-to-noise and illumination of the human organs and tissues inside thoracic cavity by imaging the multiples reflections 10. Full-azimuth, large transmitter-receiver offsets, high data density and CMUT wide frequency band are features of the 2D transducer that allow implementation of Full Waveform Inversion and Least Square Reverse Time Migration for advanced 3D imaging and 3D visualization on a cloud system 11. Reduce the time of processing, 3D imaging and 3D visualization of data acquired with 2D transducer based on compressive sensing theory by combining the interpolation and imaging in the same step.

The method to process data acquired based on compressing sensing where wavefield reconstruction of sparse data randomly distributed to the desired sampling interval is performed before the imaging step (for instance before applying Least Square Reverse Time Migration)

The method to process data acquired based on compressing sensing where wavefield reconstruction of sparse data randomly distributed to the desired sampling interval and the imaging, for instance Least Square Reverse Time Migration, are performed simultaneously. This could save significant data manipulation and time.

REFERENCES (INCORPORATED HEREIN BY REFERENCE)

1. J. Montero-Gato, L. R. Fernandez, I S. Gueridiaga, A. A. U. Berrenechea, A. A Conde, A. P. Legorburu: Ultrasound of pneumothorax in neonate: Diagnostic values of the anterior transverse plane and of mirrored ribs, January 2022, Pediatric Pulmonology
2. D. Yeh, O. Oralkan, S. Ergun, P. T. Yalkub, Integration of 2D CMUT Arrays with front-end electronics for volumetric ultrasound imaging, March 2008, IEEE transactions on ultrasonics, ferroelectrics and frequency control
3. E. J. Candes, J. Romberg, and T. Tao "Robust Uncertainty Principle: Exact Signal Reconstruction fromHighly Incomplete Frequency Information," IEEE Trans IT, 52(2), pp. 489-509, February 2006
4. Quinsac, C., A. Basarab, and D. Kouame. (2011). "Compressed Sensing of Ultrasound Images: Sampling of Spatial and Frequency Domains." 2011 8th IEEE International Symposium on Biomedical Imaging: From Nano to Macro, pp. 2013-2016.
5. B. Diarra, M. C. Robini, P. Tortoly, C. Cachard: Design of optimal 2D nongrid sparse array for medical ultrasound, June 2013, IEEE transaction on bio-medical engineering
6. O. Lopez, R. Kumar, N. Moldoveanu: Spectral Gap-Based Seismic Survey Design, January 2023, IEEE Transactions on Geoscience and Remote Sensing
7. C. L Wiley, V. W. Chen: An Element Localization Algorithm to Enable Flexible Ultrasound Array Imaging, March 2023, preprint in SSRN Electronic Journal
8. W. Chen, J. Liu, S. Lei, Z. Yang, Q. Zhang, Y. Li, L. Huang, Y. Dong, H. Zheng, D. Wu and T. Ma, 2023, Flexible Ultrasound Transducer with Embedded Optical Shape Sensing Fiber for Biomedical Imaging Applications, IEEE Transactions on Biomedical Engineering
9. X. Wu, Y. Li, C. Su, W. Lin: Ultrasound computed tomography based on full waveform inversion with source directivity calibration. April 2023, Ultrasonics 132.
10. J. T. Etgen, 3D wave equation Kirchhoff migration, 2012, SEG, Technical Abstract
11. S. Kim, Y. S. Kim, W. Chang, Efficient least-squares reverse time migration using local cross-correlation imaging condition, 2022, Journal of Geophysics and Engineering, 19, 376-388.

What is claimed is:

1. A two-dimensional ultrasound transducer, wherein the transducer comprises:
   a body for the two dimensional transducer; and
   a plurality of capacity micromachined ultrasound transducer elements distributed within the body, wherein each element is capable of transmitting and receiving sound waves;
   wherein distribution and location of the elements for the elements is determined by the steps comprising:
   (1) designing a probe that with a radius that is larger than the average size of the human ribs wherein the elements are sampled using Nyquist Shannon rule and have a substantially uniform distribution with an average interval between elements of about ½ wavelength;
   (2) transforming the probe of step (1) into an optimized circular probe comprising less elements wherein the lesser elements are distributed randomly using an optimization process comprising Spectra Gap as a cost function;
   (3) generating a grid of circle centers for the optimized circular probe wherein a number of center points in the grid and spacing between the center points are a function of the required size of the two-dimensional ultrasound transducer; and
   (4) determining an (x,y) location of each element of the two-dimensional ultrasound transducer by placing the optimized circular probe in each center point to generate the two-dimensional ultrasound transducer wherein the two-dimensional ultrasound transducer comprises a random distribution of elements.

2. The two-dimensional ultrasound transducer of claim 1 wherein the body comprises a flexible material.

3. The two-dimensional ultrasound transducer of claim 1 wherein the micromachined ultrasound transducer elements vary in size.

4. The two-dimensional ultrasound transducer of claim 3 wherein the micromachined ultrasound transducer elements are larger in size near an edge of the two-dimensional ultrasound transducer.

5. The two-dimensional ultrasound transducer of claim 3 wherein the two-dimensional ultrasound transducer is configured to (1) perform passive beamforming using phase differences of a plurality of signals received by each element without signal processing and (2) perform active beamforming with signal processing.

6. The two-dimensional ultrasound transducer of claim 1, wherein the transducer is configured to be connected via a wired connection with an administrator processor configured to receive and analyze the one or more multi-dimensional imaging data generated by the transducer.

7. The two-dimensional ultrasound transducer of claim 1, wherein the transducer is configured to generate one or more sets of multi-dimensional imaging data of one or more internal human tissues, organs, organic material, or any combination thereof.

8. The two-dimensional ultrasound transducer of claim 1, wherein the transducer produces one or more substantially full-azimuth investigations of one or more internal human tissues, organs, organic material, or any combination thereof.

9. The two-dimensional ultrasound transducer of claim 1, wherein the transducer is configured to transmit imaging data to one or more cloud servers.

10. The two-dimensional ultrasound transducer of claim 9, wherein at least a portion of the imaging data is compressed and blended either before transmission or after transmission or both to preserve data fidelity and reduce transfer time between the transducer and one or more processors.

11. The two-dimensional ultrasound transducer of claim 9, wherein the imaging data is configured to be convertible into one or more displayable multi-dimensional images.

12. The two-dimensional ultrasound transducer of claim 1 which further comprises elements capable only of transmitting sound waves.

13. The two-dimensional ultrasound transducer of claim 1 which further comprises elements capable only of receiving sound waves.

14. A system for generating ultrasound images, the system comprising:
   a two-dimensional ultrasound transducer, wherein the transducer comprises: a body for the two dimensional transducer; and a plurality of capacity micromachined ultrasound transducer elements distributed within the body, wherein each element is capable of transmitting and receiving sound waves;
   a data acquisition processor configured to receive one or more sets of imaging data from the transducer, the data acquisition processor further configured to transmit the one or more sets of imaging data over one or more express buses;
   a data storage unit configured to store at least one or more sets of imaging data;
   an administrator processor coupled to the data storage unit, the administrator processor further configured to receive the one or more sets of imaging data from the data acquisition processor over one or more express buses; and
   a server configured to receive the one or more sets of imaging data over a network, wherein the server is further configured to:
      convert the one or more multi-dimensional imaging data into one or more displayable images; and
      transmit the one or more displayable multi-dimensional images;
   wherein the elements are distributed across the transducer according to a matrix M defined by one or more x, y locations; and
   wherein the elements are distributed across the transducer according to a spectral gap defined as a ratio between a first and second largest values of the matrix M, wherein the spectral gap is analyzed, by a processor, to be determined to be of a sufficient size, wherein the analysis comprises:
      calculating a spectral gap for an ideal transducer, SGi;
      calculating a spectral gap for one or more distributed elements, SGr,
      comparing the values and calculating the difference SGi-SGr, and reiterating the process until the difference SGi-SGr is reduced to maximize the spectral gap for the distribution of the elements.

15. The system of claim 14, wherein the data storage unit is configured for both short-term and long-term storage of the multi-dimensional imaging data and the one or more multi-dimensional images.

16. The system of claim 14, wherein the server is a cloud server configured to convert and transmit the images in real time.

* * * * *